US006248526B1

(12) United States Patent
Weimer

(10) Patent No.: US 6,248,526 B1
(45) Date of Patent: Jun. 19, 2001

(54) LABELED PRIMER FOR USE IN AND DETECTION OF TARGET NUCLEIC ACIDS

(75) Inventor: Thomas Weimer, Gladenbach (DE)

(73) Assignee: Aventis Behring, GmbH, Marburg (DE)

(*) Notice: Subject to any disclaimer, the term of this patent is extended or adjusted under 35 U.S.C. 154(b) by 0 days.

(21) Appl. No.: 09/210,657

(22) Filed: Dec. 14, 1998

(30) Foreign Application Priority Data

Dec. 15, 1997 (DE) ............................................... 197 55 642
Feb. 19, 1998 (DE) ............................................... 198 06 850
Aug. 3, 1998 (DE) ............................................... 198 34 913

(51) Int. Cl.$^7$ .................................................... C12Q 1/68
(52) U.S. Cl. ................. 435/6; 435/6; 435/91.5; 435/91.52; 435/810; 435/183; 435/184; 435/194; 435/91.2; 536/24.31; 536/24.33; 935/8; 935/78
(58) Field of Search ............................ 435/6, 91.5, 91.52, 435/810, 183, 184, 194, 91.2; 536/24.31, 24.33; 935/8, 78

(56) References Cited

U.S. PATENT DOCUMENTS

| 5,391,480 | 2/1995 | Davis et al. . | |
|---|---|---|---|
| 5,804,375 | 9/1998 | Gelfand et al. . | |
| 5,804,380 | * | 9/1998 | Harley et al. ............................. 435/6 |

FOREIGN PATENT DOCUMENTS

WO 90/11372  10/1990  (WO) .
WO 90/12115  10/1990  (WO) .
WO 92/02638  2/1992  (WO) .

OTHER PUBLICATIONS

H. A. Erlich et al., "Recent Advances in the Polymerase Chain Reaction", Science, vol. 252, pp. 1643–1651, 1991.

L. Stryer, "Fluorescence Energy Transfer as a Spectroscopic Ruler", Ann. Rev. Biochem., vol. 47, pp. 819–846, 1978.

K. J. Livak, et al., "Oligonucleotides with Fluorescent Dyes at Opposite Ends Provide a Quenched Probe System Useful for Detecting PCR Product and Nucleic Acid Hybridization", PCR Methods and Applications, vol., 4, pp. 357–362, 1995.

M. Ishizawa et al., "Simple Procedure of DNA Isolation from Human Serum", Nucleic Acids Research, vol. 19, No. 20, p. 5792, 1991.

* cited by examiner

Primary Examiner—W. Gary Jones
Assistant Examiner—Janell E. Taylor
(74) Attorney, Agent, or Firm—Finnegan, Henderson, Farabow, Garrett & Dunner

(57) ABSTRACT

A labeled primer for use in detection of nucleic acid is described, which primer is labeled at the two ends of the oligonucleotide strand with a reporter dye molecule and a quencher molecule, and in which labeled primer, at least one base at the 3' end is deliberately not complementary to the nucleic acid sequence to be amplified. A process for detecting a nucleic acid sequence using a labeled primer is also described. The process can also be used in amplification processes.

22 Claims, 1 Drawing Sheet

SEQUENCE LISTING

<160> NUMBER OF SEQ ID NOS: 6

<210> SEQ ID NO 1
<211> LENGTH: 21
<212> TYPE: DNA
<213> ORGANISM: Hepatitis C virus

<400> SEQUENCE: 1
gcgtctagcc atggcgttag t                                              21

<210> SEQ ID NO 2
<211> LENGTH: 29
<212> TYPE: DNA
<213> ORGANISM: Hepatitis C virus

<400> SEQUENCE: 2
ccacaaggcc tttcgcgacc caacttact                                      29

<210> SEQ ID NO 3
<211> LENGTH: 29
<212> TYPE: DNA
<213> ORGANISM: Hepatitis C virus
<220> FEATURE:
<221> NAME/KEY: misc_feature
<222> LOCATION: (1)
<223> OTHER INFORMATION: 5'-reporter
<220> FEATURE:
<221> NAME/KEY: misc_feature
<222> LOCATION: (29)
<223> OTHER INFORMATION: 3'-quencher

<400> SEQUENCE: 3
ccacaaggcc tttcgcgacc caacttact                                      29

<210> SEQ ID NO 4
<211> LENGTH: 22
<212> TYPE: DNA
<213> ORGANISM: Hepatitis B virus

<400> SEQUENCE: 4
aatccacact ccgaaagaca cc                                             22

<210> SEQ ID NO 5
<211> LENGTH: 20
<212> TYPE: DNA
<213> ORGANISM: Hepatitis B virus

<400> SEQUENCE: 5
gcctccaagc tgtgccttgg                                                20

<210> SEQ ID NO 6
<211> LENGTH: 24
<212> TYPE: DNA
<213> ORGANISM: Hepatitis B virus
<220> FEATURE:
<221> NAME/KEY: misc_feature
<222> LOCATION: (1)
<223> OTHER INFORMATION: 5'-reporter
<220> FEATURE:
<221> NAME/KEY: misc_feature -continued

```
<222> LOCATION: (24)
<223> OTHER INFORMATION: 3'-quencher

<400> SEQUENCE: 6
gcctccaagc tgtgccttgg tgaa                                          24
```

LABELED PRIMER FOR USE IN AND DETECTION OF TARGET NUCLEIC ACIDS

The invention relates to a labeled primer for nucleic acid amplification reactions (for example, the polymerase chain reaction) and to a process for detecting a nucleic acid sequence by means of a nucleic acid amplification process in which a labeled primer is used.

As is known, the polymerase chain reaction (PCR) is a very effective method for detecting small quantities of a known nucleic acid sequence in a sample (Erlich H. A., Gelfand, D. Sninsky JJ. (1991), Science, 252, pp. 1643–1651, which publication is incorporated herein by reference; PCR Protocols. Current methods and applications (1993) edited by B. A. White, Humana Press, Totowa, N.J., ISBN 0-89603-244-2, which publication is incorporated herein by reference). If the sequence of, for example, a viral DNA is already known, it is possible to synthesize a pair of primers which are complementary to regions on opposite single strands and which flank a target nucleic acid sequence of interest (e.g., a DNA sequence). Under PCR conditions, which are known per se, the primers can be annealed, or hybridized, to the target DNA, and a number of reaction cycles, normally more than 30, can then be used to produce large quantities of a specific DNA in vitro. The PCR cycles amplify a DNA fragment, which is of a specific size and which is composed of the lengths of the two primers plus the length of the DNA between them, when the target DNA is present in the sample. The PCR technique is so sensitive that it can be used to detect extraordinarily small quantities of a DNA with a high degree af reliability.

International Patent Application WO 92/02638, herein incorporated by reference, discloses a process for detecting a DNA sequence, in which process a sample, which contains or is suspected to contain the DNA to be detected (as a single strand), i.e., the target DNA, is hybridized with two different primers, i.e., the forward primer and the reverse primer, which flank the target DNA strand to be amplified. A labeled oligonucleotide probe, which is provided in a preferred embodiment of WO 92/02638 with a fluorescent dye system as label at both the 5' end and at the 3' end of the probe, is also employed in the reaction. This labeled probe is selected such that it hybridizes to the target DNA. In the fluorescent dye system, the fluorescence of one of the dyes, the reporter dye, is decreased ("quenched") by the proximity of the second molecule, i.e. the quencher, by a process known as fluorescence resonance energy transfer (FRET) (Stryer, L. 1978; Fluorescence energy transfer as a spectroscopic ruler. Ann. Rev. Biochem. 47: 819–846, which is incorporated herein by reference). A labeled probe, has, as an example, the following sequence:

5'FAM-TGG TGG TCT GGG ATG AAG GTA TTA TT-TAMRA3' wherein FAM represents the reporter dye, and TAMRA represents the quencher dye. A probe having the sequence and label can be ordered and obtained from a number of companies and is intended for use in a 5'-nuclease assay, i.e. the TaqMan® assay, which is described in detail by Livak K. J., Flood S. J. A., Marmaro, J., Giusti W., Deetz K., Oligonucleotides with fluorescent dyes at opposite ends provide a quenched probe system useful for detecting PCR product and nucleic acid hybridization, PCR Method and Appl, 1995; 4:357–362, which is incorporated herein by reference.

The special feature of this quenched probe system is that the fluorescence of the reporter dye (FAM), which is attached to the 5' end of the probe, is reduced by proximity to the quencher dye (TAMRA), which is attached to the 3' end of the probe, see above.

As the new DNA strand is formed under the influence of a suitable, preferably thermostable, DNA polymerase, e.g. the TaqDNA polymerase, the polymerase not only displaces the labeled probe from the single strand but also, by means of its 5'→3' nuclease activity, degrades the probe and thereby releases the two fluorescent dyes. The fluorescence of the reporter dye is now no longer suppressed by the quencher dye and increases. A fluorescence spectrometer can then be used to measure the fluorescence at the wavelength of the reporter dye, which is proportional to the quantity of newly formed DNA.

The fact that a labeled probe is required, in addition to the forward primer and the reverse primer, in order to be able to observe or measure the amplification of the DNA segment to be detected has to be regarded as a disadvantage of this method. Therefore, a need arose to simplify this known process.

It has now been found that the use of an additional labeled probe in the polymerase chain reaction is unnecessary if at least one of the two primers is labeled, e.g., with an interactive label system in which care is taken to ensure that the labeled primer contains at least one nucleotide that is not complementary to the DNA strand to be amplified, i.e., a portion of the primer is deliberately mismatched.

The invention therefore provides a labeled primer and a process for the detection of a target nucleic acid. The labeled primer is deliberately mismatched in at least one nucleotide, and preferably two to five or more nucleotides, at the 3' end of the primer. The labeled primer is incubated with a sample that contains or is suspected to contain the target nucleic acid or DNA under conditions sufficient to allow annealing or hybridization and said sample is subsequently exposed to nucleic acid polymerase having a 3' to 5' proofreading or functionally equivalent nuclease activity, or a mixture of enzymes having such proofreading activity, under conditions sufficient to permit said 3' to 5' proofreading activity to cleave said forward and/or reverse primer in said 3' mismatched portion, thereby releasing said label or part of the label system. In a preferred embodiment, the labeled primer is used in a process of nucleic acid amplification to detect the target nucleic acid.

In another preferred embodiment, a label or label system is attached to the primer at or near its 3' end and has an interactive label. For example, the interactive label system has a reporter dye molecule and a quencher molecule. At least one, and preferably at least the last two to five, or more, nucleotides at the 3' end of the primer are deliberately mismatched to the DNA or nucleic acid sequence to be amplified. The label or part of a label system is attached to the 3'-terminal mismatched portion, preferably to the 3' end nucleotide. The length of the unpaired region is selected and/or optimized by methods known to those skilled in the art for the particular label and particular polymerase used. Such a labeled primer is not able to undergo complete base pairing at its 3'-end with the DNA sequence to be amplified. Under the influence of the polymerase employed for the amplification, which possesses proof-reading or nuclease properties equivalent to such, the unpaired bases of the labeled primer, together with the label, e.g., the reporter dye molecule or quencher molecule, are released by the 3'→5' nucleolytic activity of the polymerase before the actual elongation reaction takes place. In the process, the quencher is removed from spatial proximity to the reporter dye. The fluorescence of the reporter dye therefore increases, indicating presence of a target nucleic acid. The most preferred embodiment is illustrated in FIG. 1.

The invention also relates to a process for detecting a target nucleic acid by means of nucleic acid amplification, in which process one of the primers possesses the abovementioned features. In the amplification, for which it is possible to use one or more thermostable DNA polymerases, at least one of which must also have proof-reading or functionally equivalent nuclease properties, the unpaired bases of the labeled primer, together with the label or part of a label system, e.g., a reporter dye which is attached to the labeled primer, are then released, resulting in a signal increase, e.g. fluorescence increasing at the wavelength of the reporter dye.

In the novel process, the forward primer or the reverse primer, or both, can be labeled with the reporter and quencher molecules each as described above. While the quencher dye is liberated into the reaction solution, the newly formed nucleic acid segment also carries the fluorescent reporter dye, in addition to the remainder of the primer. This is the preferred procedure for quantitative applications. However, labeling with the quencher and reporter dye can also be effected equally well in the converse manner, so that the reporter dye is liberated into the solution, and the newly formed nucleic acid segment carries the quencher. If several parameters are to be simultaneously detected in parallel (multiplexing), it is then expedient to select reporter dyes which can be detected in parallel. The method of the invention is very well-suited for multiplexing.

The 3'-end of a primer is labeled or attached to the part of a label system, as described below, by incorporating moieties detectable by spectroscopic, photochemical, immunochemical, or chemical means. The method of linking or conjugating the label to the primer depends, of course, on the type of label(s) used and the position of the label on the primer.

A variety of labels that would be appropriate for use in the invention, as well as methods for their inclusion in the primer, are known in the art and include, but are not limited to, enzymes (e.g., alkaline phosphatase and horseradish peroxidase (HRP)) and enzyme substrates, radioactive atoms, fluorescent dyes, chromophores, chemiluminescent labels, electrochemiluminescent labels, such as Origen™ (Igen), ligands having specific binding partners, or any other labels that may interact with each other to enhance, alter, or diminish a signal. When the amplification method used is PCR and is practiced using a thermal cycler instrument, the label must be able to survive the temperature cycling required in this automated process.

Among radioactive atoms, $^{32}P$ is preferred. Methods for introducing $^{32}P$ into nucleic acids are known in the art, and include, for example, 5' labeling with a kinase, or random insertion by nick translation. Enzymes are typically detected by their activity. "Specific binding partner" refers to a protein capable of binding to a specific monoclonal antibody specific. Other specific binding partners include biotin and avidin or streptavidin, IgG and protein A, and numerous other receptor-ligand couples known in the art.

The above description is not meant to categorize the various labels into distinct classes, as the same label may serve in several different modes. For example, $^{125}I$ may serve as a radioactive label or as an electron-dense reagent. HRP may serve as enzyme or as antigen for a monoclonal antibody. Further, one may combine various labels to achieve a desired effect. For example, one might label a primer with biotin, and detect the presence of the primer with avidin labeled with $^{125}I$, or with an anti-biotin monoclonal antibody labeled with HRP. Other permutations and possibilities will be readily apparent to those of ordinary skill in the art, and are considered as equivalents within the scope of the instant invention.

Fluorophores for use in constructing labeled primers of the invention include rhodamine and derivatives, such as Texas Red, fluorescein and derivatives thereof, such as 5-bromomethyl fluorescein, Lucifer Yellow, IAEDANS, 7-Me$_2$N-coumarin-4-acetate, 7-OH-4-CH$_3$-coumarin-3-acetate, 7-NH$_2$-4-CH$_3$-coumarin-3-acetate (AMCA), monobromobimane, pyrene trisulfonates, such as Cascade Blue, and monobromotrimethyl-ammoniobimane. In general, fluorophores with wide Stokes shifts are preferred, to allow using fluorometers with filters rather than monochromometers, and to increase the efficiency of detection. However, the particular label(s) chosen preferably has (have) some quality (e.g., the reporter-quencher relationship) that allows detection in a homogeneous assay system.

Detection or verification of the label in the processes disclosed is accomplished by a variety of methods and is dependent on the source of the label(s) employed. In a preferred embodiment of the invention, the increase of fluorescence is measured using a suitable fluorometer.

In yet another preferred embodiment of the instant invention, two interactive labels on a single primer are used as a reporter-quencher label system. Examples of reporter molecules are B-carboxy-fluorescein (FAM), Tetrachloro-6-carboxy-fluorescein (TET), and 6-Carboxy-X-carboxy-tetra-methyl-Rhodamin (ROX). Examples of quencher molecules are 6-Carboxy-tetramethyl-Rhodamin (TAMRA) and 4-(4'-Dimethylamino-phenylazo) benzoic acid (DABCYL). Whereas TAMRA is a fluorescent dye, DABCYL is not.

Different polymerases can be employed for the amplification reaction. If the polymerase which is used for the amplification has proof-reading or functionally equivalent nuclease properties, a single polymerase can be used in the reaction (e.g. ULTma® DNA polymerase, which is produced for Perkin Elmer by Roche Molecular Systems, Branchburg, N.J., USA). Otherwise, it is necessary to use a mixture of several polymerases. For example, TaqDNA polymerase can be used in combination with a polymerase having 3'→5' nuclease activity. Tli DNA polymerase (Promega Corporation, Madison, Wis., USA) or Vent DNA polymerase (New England Biolabs, Beverly, Mass., USA) are suitable thermostable polymerases possessing 3'→5' nuclease activity. ACCUTAQ™ LA DNA Polymerase Mix, sold by SIGMA Corp (see Annex 1), is very well-suited for use in the instant invention. Such a mix and related enzyme compositions are described in Example 6 of U.S. Pat. No. 5,436,149, which is herewith incorporated by reference in its entirety.

The novel processes are based on recognition of the fact that the unpaired bases of the primer are a point of attack for the polymerase, which possesses a proof-reading and nuclease function. The thermostable DNA polymerases which are employed possess a 3'→5' nuclease activity, preferably 3'→5' exonuclease activity, which results in the nonhybridized bases, together with either the quencher or reporter molecule, being released.

The primers used in the novel processes comprise preferably oligonucleotides of 18 to 25 bases in the paired or matching region as related to the target nucleic acid for average G/C and A/T ratios, but are somewhat longer in case of more A/T base pairings, and conform to the general methodology for making primers as disclosed in the PCR art above.

The processes disclosed are valuable, in particular, for their simplicity in comparison to the prior art, e.g., WO 92/02638, because in the disclosed processes, only two oligonucleotides (primers) are required for implementing the nucleic acid amplification. This is advantageous when, for example, conserved nucleic acid segments have to be amplified for detecting variable target sequences, such as those of viruses, or several parameters, e.g., viral parameters, are to be detected simultaneously.

In addition, the method described herein is very well-suited for quantitative amplification, since the increase in fluorescence is directly proportional to the quantity of amplified DNA.

BRIEF DESCRIPTION OF THE DRAWING

FIG. 1 depicts a cycle of the claimed process in which:
A denotes the forward primer with its unpaired 3' end;
B denotes the reverse primer;
R denotes the reporter molecule; and
Q denotes the quencher molecule.

Figure 1:
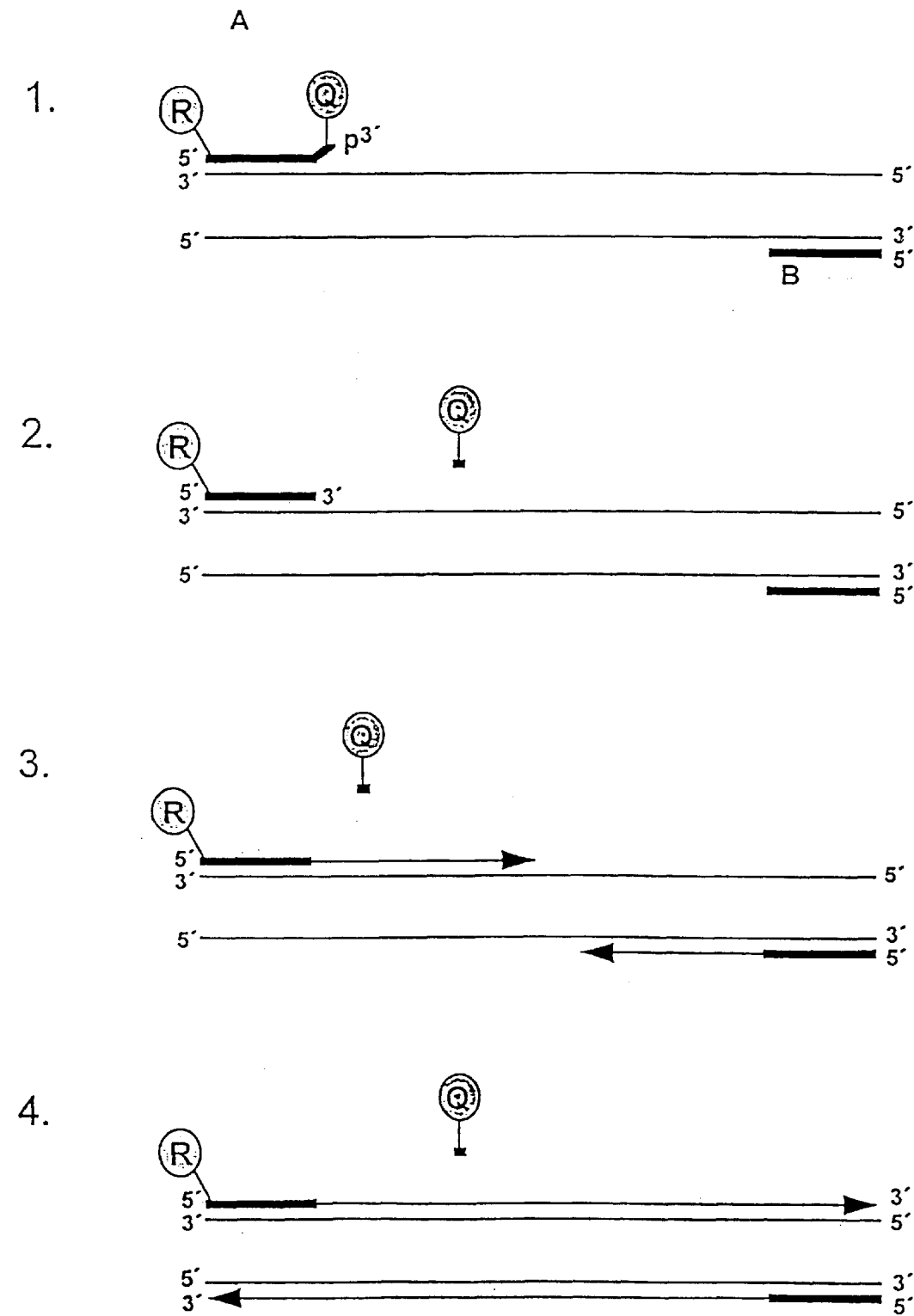
FIG. 1 is a diagram showing the labeled primer and its use in the process of the invention.

In Step 1, the primer anneals or hybridizes to the complementary portion on the target nucleic acid. The 3' end of the primer remains unpaired, since it is not complementary to the target nucleic acid.

In Step 2, an enzyme possessing proof-reading or functionally equivalent nuclease functions removes the unpaired 3' end and the attached quencher molecule.

In Steps 3 and 4, the nucleic acid strands are elongated. The reporter molecule is attached to the elongated strands, and is no longer in proximity to the quencher molecule, thus increasing the fluorescent signal.

The most preferred embodiments of the invention are processes in which PCR is the nucleic acid amplification method and wherein the 3' mismatched primer is labeled by a quenchable fluorescent dye molecule and a quencher molecule, where at least one of said molecules is at or within the mismatched 3' end of said primer. Where an RNA target is to be detected, reverse transcription of the target RNA into DNA is performed preceding amplification via PCR. If the target nucleic acid is abundant, a single PCR using labeled primer according to protocols known to those skilled in the art is preferable (See Example 2). If high sensitivity of target nucleic acid detection is desired, a first PCR amplifying the target nucleic acid using non-labeled primers that are completely complementary to the target nucleic acid, may be performed. A second amplification of the target nucleic acid via nested PCR using the labeled primers of the invention then follows. In especially the second amplification (nested PCR), it has been found that the addition of unlabeled primer with or without the 3' mismatching portion or tail can be an advantage, in that it may render the amplification more efficient, and allows for reduction of the labeled primer.

Reagents employed in the methods of the invention can be packaged into diagnostic kits. Diagnostic kits include the labeled primers in separate containers. If the primer(s) is (are) unlabeled, the specific labeling reagents may also be included in the kit. The kit may also contain other suitably packaged reagents and materials needed for sample preparation and amplification, for example, extraction solutions for the target nucleic acid, buffers, dNTPs, and/or polymerizing means, and reagents for detection analysis, for example, enzymes and solid phase extractants, as well as instructions for conducting the assay. Another object of the invention is the various reaction mixtures useful for the processes disclosed for detecting a target nucleic acid in a sample. Samples may be body fluids of human or animal origin, or extracts of any body component of interest. Preferred samples are blood, plasma or any products resulting from same.

The invention is illustrated but not limited by the examples that follow:

EXAMPLE 1

This example is for applications which require high sensitivity. In this case, a first round of amplification preceded a second PCR performed with the labeled primer.

Detection of Hepatitis C virus RNA was carried out as follows. RNA was extracted using standard methods (See, e.g., Ishizawa M., Kobayashi Y., Miyamura T., Matsuma, S: Simple procedure of DNA isolation from human serum. Nucl. Acids Res, 1991; 19:5792, which publication is incorporated herein by reference). The isolated RNA was reverse-transcribed and amplified using standard methods (RT-PCR). The second amplification and detection reaction was set up as follows:

5 µl of 10×ULTma buffer (100 mM Tris-HCl, pH 8.8., 100 mM KCl, 0.02% Tween 20) (Perkin-Elmer), 7 µl of 25 mM $MgCl_2$, 8 µl of primer 1 (see SEQ ID No. 1 of the sequence listing) (10 pmol/µl), 4 µl of primer 2 (see SEQ ID No. 2 of the sequence listing) (10 pmol/µl), 0.25 µl of primer 3 (see SEQ ID No. 3 of the sequence listing) (10 pmol/µl), 2 µl of dNTPs (10 mM) and 0.5 µl of ULTma DNA polymerase, which possesses a proof-reading function (Perkin-Elmer, 6 units/µl) was added to 5 µl of the RT-PCR reaction, and 18.25 µl of water was added to the reaction mixture. The sample was then subjected to the following thermocycles:
1. initial denaturation for 1 minute at 90° C.;
2. 35 cycles, of, in each case, 28 seconds at 94° C. (for denaturation), and 1 minute at 56° C. (for annealing and extension); and
3. cooling at 4° C. until evaluated.

The results were evaluated by fluorescence spectrometry, in which fluorescence was measured at the reporter wavelength (518 nm for FAM). A threshold value based on the fluorescence of negative controls (reactions carried out using labelled probe, but no target nucleic acid) was calculated, and used to calculate unknown values.

EXAMPLE 2

This example is for applications which do not require high sensitivity. In this example, a single amplification reaction containing the labeled primer was carried out.

Detection of Hepatitis B virus DNA in seropositive patients was carried out as follows. Viral DNA was extracted from a patient sample using standard methods (see, e.g., Ishizawa M., Kobayashi Y., Miyamura T., Matsuma, S: Simple procedure of DNA isolation from human serum. Nucl. Acids Res. 1991; 19:5792). The reaction was set up as follows:

5 µl of 10×ULTma buffer (100 mM Tris-HCl, pH 8.8, 100 mM KCl, 0.02% Tween 20) (Perkin-Elmer), 7 µl of 26 mM $MgCl_2$, 8 µl of primer 4 (see SEQ ID No. 4 of the sequence listing) (10 pmol/µl), 4 µl of primer 5 (see SEQ ID No. 5 of the sequence listing) (10 pmol/µl), 0.25 µl of primer 6 (see SEQ ID No. 6 of the sequence listing) (10 pmol/µl), 2 µl of dNTPs (10 mM) and 0.5 µl of ULTma DNA polymerase, which possesses a proof-reading function (Perkin-Elmer, 6 units/µl) were added to 5 µl of the extracted DNA (i.e., the target nucleic acid), and 18.25 µl of water was added to the reaction mixture. The sample was then subjected to the following thermocycles:
1. initial denaturation for 1 minute at 90° C.;
2. 35 cycles, of, in each case, 28 seconds at 94° C. (for denaturation) and 1 minute at 58° C. (for annealing and extension); and
3. cooling at 4° C. until evaluated.

Evaluation of results was done as described in example 1.

In both examples 1 and 2, the reporter molecule was FAM and the quencher molecule was TAMRA.

What is claimed is:

1. A process for the detection of a target nucleic acid in a sample comprising single-stranded DNA, said process comprising:
   (a) contacting said sample with a forward and/or reverse primer, wherein at least one primer carries a label or part of a label system in a 3' terminal portion of said primer which is deliberately mismatched relative to the target nucleic acid, said mismatched portion amounting to at least one nucleotide, under conditions sufficient to allow hybridization of the complementary portions of said forward and/or reverse primer and said target nucleic acid;
   (b) subsequently exposing said sample to nucleic acid polymerase having a 3' to 5' proofreading or functionally equivalent nuclease activity, or a mixture of enzymes having such proofreading activity, under conditions sufficient to permit said 3' to 5' proofreading activity to cleave said forward and/or reverse primer in said 3' mismatched portion, thereby releasing said label or part of a label system;
   (c) detecting and/or measuring the release of said label or part of a label system.

2. A process according to claim 1, wherein the target nucleic acid is amplified and thereby more label or part of a label system is released.

3. A process according to claim 1 or claim 2, wherein the amplification is performed by PCR.

4. A process according to claim 3, wherein said amplification is RT-PCR, and said target nucleic acid is RNA.

5. A process according to claim 3, wherein the label is a reporter-quencher molecule pair linked to the 3' and 5' terminal regions of the forward and/or the reverse primer.

6. A process according to claim 5, wherein the reporter molecule is on the mismatched 3' part of the primer and the quencher molecule is on the mismatched part of said primer at a suitable distance from the reporter molecule.

7. A process according to claim 5, wherein the quencher molecule is on the mismatched 3' part of the primer and the reporter molecule is on the matched part of said primer at a suitable distance from the quencher molecule.

8. A process accoding to claim 1, wherein said nucleic acid polymerase or said mixture of enzymes are thermostable.

9. A process according to claim 1, wherein a multiplicity of targets are detected simultaneously by suitable selection or primers and respective label systems.

10. A process according to claim 1, wherein the sample is animal or human body fluid.

11. A process according to claim 10, wherein the sample is plasma.

12. A kit for the detection of a target nucleic acid in a sample comprising labeled primers used in the process of claim 1, and a suitable nucleic acid polymerase or mixture of enzymes.

13. A kit as claimed in claim 12 wherein the primers detect target viral nucleic acids.

14. A reaction mixture for detecting a target nucleic acid which reaction mixture comprises labeled primers used in the process of claim 1 and a suitable nucleic acid polymerase or mixture of enzymes.

15. A reaction mixture for detecting a target nucleic acid which reaction mixture comprises labeled primers the used in the process of claim 2, and a suitable nucleic acid polymerase or mixture of enzymes.

16. A reaction mixture for detecting a target nucleic acid which reaction mixture comprises labeled primers used in the process of claim 5, and a suitable nucleic acid polymerase or mixture of enzymes.

17. A reaction mixture for detecting a target nucleic acid which reaction mixture comprises labeled primers used in the process of claim 6, and a suitable nucleic acid polymerase or mixture of enzymes.

18. A reaction mixture for detecting a target nucleic acid which reaction mixture comprises labeled primers used in the process of claim 7, and a suitable nucleic acid polymerase or mixture of enzymes.

19. A reaction mixture for detecting a target nucleic acid which reaction mixture comprises labeled primers used in the process of claim 8, and a suitable nucleic acid polymerase or mixture of enzymes.

20. The process according to claim 1, wherein said mismatched portion is 2 or more nucleotides.

21. The process according to claim 1, wherein said mismatched portion is 2 to 5 nucleotides.

22. A process according to claim 7, wherein the reporter molecule is at the 5' end.

* * * * *

UNITED STATES PATENT AND TRADEMARK OFFICE
CERTIFICATE OF CORRECTION

PATENT NO. : 6,248,526 B1
DATED : June 19, 2001
INVENTOR(S) : Weimer

It is certified that error appears in the above-identified patent and that said Letters Patent is hereby corrected as shown below:

<u>Column 9,</u>
Line 51, "accoding" should read -- according --.

<u>Column 10,</u>
Line 29, after "labeled primers", delete "the".

Signed and Sealed this

Third Day of September, 2002

*Attest:*

*Attesting Officer*

JAMES E. ROGAN
*Director of the United States Patent and Trademark Office*